(12) United States Patent
Vaillant et al.

(10) Patent No.: US 11,037,280 B2
(45) Date of Patent: Jun. 15, 2021

(54) SYSTEM AND METHOD FOR SIMULATING BILATERAL INJECTION OF CONTRAST AGENT INTO A PATIENT

(71) Applicant: GE PRECISION HEALTHCARE LLC, Wauwatosa, WI (US)

(72) Inventors: Régis Vaillant, Villebon sur Yvette (FR); Liliane Ramus, Versailles (FR); Sophie Amelot, Marly-le-Roi (FR)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

(21) Appl. No.: 16/299,595

(22) Filed: Mar. 12, 2019

(65) Prior Publication Data
US 2020/0294213 A1    Sep. 17, 2020

(51) Int. Cl.
*G06T 5/50* (2006.01)
*A61B 6/00* (2006.01)
*G06T 7/00* (2017.01)

(52) U.S. Cl.
CPC .............. *G06T 5/50* (2013.01); *A61B 6/481* (2013.01); *A61B 6/504* (2013.01); *A61B 6/5241* (2013.01); *G06T 7/00* (2013.01); *A61B 6/547* (2013.01); *A61B 6/563* (2013.01); *G06T 2207/10116* (2013.01); *G06T 2207/20221* (2013.01)

(58) Field of Classification Search
CPC ... G06T 5/50; G06T 7/00; G06T 2207/10116; G06T 2207/20221; A61B 6/481; A61B 6/504; A61B 6/5241; A61B 6/547; A61B 6/563

USPC .......................................................... 382/128
See application file for complete search history.

(56) References Cited

U.S. PATENT DOCUMENTS

| | | |
|---|---|---|
| 6,215,849 B1 | 4/2001 | Lienard et al. |
| 6,944,265 B2 | 9/2005 | Warp et al. |
| 7,440,599 B2 | 10/2008 | Kato |
| 9,449,580 B2 | 9/2016 | Kotian et al. |
| 10,080,539 B2 | 9/2018 | Ranjan |
| 2007/0183637 A1* | 8/2007 | Kreuzer ................ A61B 6/504 382/128 |
| 2008/0221440 A1* | 9/2008 | Iddan ................ A61B 5/02007 600/424 |

(Continued)

FOREIGN PATENT DOCUMENTS

| | | |
|---|---|---|
| EP | 1901232 B1 | 3/2011 |
| WO | 2006010609 | 2/2006 |

(Continued)

OTHER PUBLICATIONS

EP application 20161674.5 filed Mar. 6, 2020—Search Report dated Aug. 10, 2020, 7 pages.

*Primary Examiner* — Michael R Neff

(57) ABSTRACT

A system for simulating bilateral injection of contrast agent into a patient is provided. The system includes an x-ray imaging device and a controller. The controller is operative to: acquire a first image set of a first blood vessel having contrast agent therein via the x-ray imaging device; acquire a second image set of a second blood vessel having contrast agent therein via the x-ray imaging device; and generate a third image set based at least in part on the first image set and the second image set. The third image set includes at least one composite image that depicts both the first blood vessel and the second blood vessel.

14 Claims, 6 Drawing Sheets

(56) References Cited

U.S. PATENT DOCUMENTS

| | | | |
|---|---|---|---|
| 2010/0094124 A1* | 4/2010 | Schoonenberg | G06T 7/33 |
| | | | 600/424 |
| 2010/0172472 A1 | 7/2010 | Ermes | |
| 2011/0235885 A1* | 9/2011 | Rauch | A61B 6/504 |
| | | | 382/131 |
| 2012/0020462 A1 | 1/2012 | Hansis | |
| 2014/0039303 A1* | 2/2014 | Kanzaki | A61B 6/541 |
| | | | 600/424 |
| 2019/0304592 A1* | 10/2019 | Ma | G06T 17/00 |

FOREIGN PATENT DOCUMENTS

| WO | 2012016844 | | 4/2012 |
|---|---|---|---|
| WO | 2015044433 | A1 | 4/2015 |

\* cited by examiner

SYSTEM AND METHOD FOR SIMULATING BILATERAL INJECTION OF CONTRAST AGENT INTO A PATIENT

BACKGROUND

Technical Field

Embodiments of the present invention relate generally to diagnostic medical imaging, and more specifically, to a system and method for simulating bilateral injection of contrast agent into a patient.

Discussion of Art

Interventional cardiology is a field of medicine that involves detecting, clearing, and/or stenting coronary arteries that have become obstructed due to the buildup of plaque, e.g., deposits of cholesterol, fats and/or other substances, on the side walls of coronary arteries. In many interventional cardiology procedures, diagnosis of the degree and type of coronary occlusion, as well as navigation of various tools to mitigate the occlusion, e.g., stents, balloons, etc., is accomplished by injecting contrast agent into one or more coronary arteries via catheters and recording the flow of the contrast agent within the coronary arteries via x-ray imaging.

When a coronary artery becomes completely blocked, a situation known as a Chronic Total Occlusion, a physician may attempt to clear and/or stent the occlusion by performing a retrograde navigation inside the coronary branch. A retrograde navigation usually involves introducing a guidewire into a non-blocked coronary artery, and subsequently navigating the guidewire antegrade within the non-blocked coronary artery, through a collateral artery connecting the non-blocked and completely blocked coronary arteries, and into the distal end of the completely blocked coronary artery in order to approach the occlusion from the downstream side. As will be appreciated, such a procedure is generally considered complex and typically requires planning of the guidewire path prior to insertion of the guidewire into the non-blocked coronary artery. As will be understood, however, contrast agent injected into a completely blocked coronary artery is unable to flow past the occlusion, thus making it difficult to determine the length and/or size of the occlusion, as well as the shape of the coronary artery downstream of the occlusion.

As coronary arteries are connected via one or more collateral arteries, contrast agent injected into a coronary artery that is not completely blocked will flow into a completely blocked artery at a point downstream of the occlusion. Thus, present approaches of diagnostically imaging the coronary arteries of a patient, for the purpose of planning a guidewire path for a retrograde navigation, typically involve injecting two interconnected coronary arteries, one being completely blocked and one not, with contrast agent and imaging them at the same time in a procedure commonly referred to as a bilateral injection. Injection of the completely blocked coronary artery will reveal the shape of the coronary artery up to the occlusion, and injection of the non-completely blocked and connected coronary artery will reveal the shape of the completely blocked coronary artery downstream of the occlusion. Simultaneous injection of two coronary arteries, however, is itself usually considered a complex procedure as the physician must simultaneously track and navigate two catheters, one in each coronary artery, used to inject the contrast agent.

While some present approaches of diagnostically imaging coronary arteries stagger contrast agent injections into two coronary arteries, such approaches result in two separate video sequences that must both be viewed in a side-by-side manner. The cardiac phase of the coronary arteries in such side-by-side video feeds, however, is usually unsynchronized which, in turn, often makes it difficult to view the collateral artery connection sites between the two coronary arteries.

What is needed, therefore, is an improved system and method for simulating bilateral injection of contrast agent into a patient.

BRIEF DESCRIPTION

In an embodiment, a system for simulating bilateral injection of contrast agent into a patient is provided. The system includes an x-ray imaging device and a controller. The controller is operative to: acquire a first image set of a first blood vessel having contrast agent therein via the x-ray imaging device; acquire a second image set of a second blood vessel having contrast agent therein via the x-ray imaging device; and generate a third image set based at least in part on the first image set and the second image set. The third image set includes at least one composite image that depicts both the first blood vessel and the second blood vessel.

In another embodiment, a method for simulating bilateral injection of contrast agent into a patient is provided. The method includes injecting a first blood vessel with contrast agent; acquiring a first image set of the first blood vessel via an x-ray imaging device; and injecting a second blood vessel with contrast agent. The method further includes: acquiring a second image set of the second blood vessel via the x-ray imaging device; and generating, via a controller, a third image set based at least in part on the first image set and the second image set. The third image set includes at least one composite image that depicts both the first blood vessel and the second blood vessel.

In still yet another embodiment, a non-transitory computer readable medium storing instructions is provided. The stored instructions adapt a controller to: acquire a first image set of a first blood vessel having contrast agent therein; acquire a second image set of a second blood vessel having contrast agent therein; and generate a third image set based at least in part on the first image set and the second image set. The third image set includes at least one composite image that depicts both the first blood vessel and the second blood vessel.

DRAWINGS

The present invention will be better understood from reading the following description of non-limiting embodiments, with reference to the attached drawings, wherein below:

Figure 1:
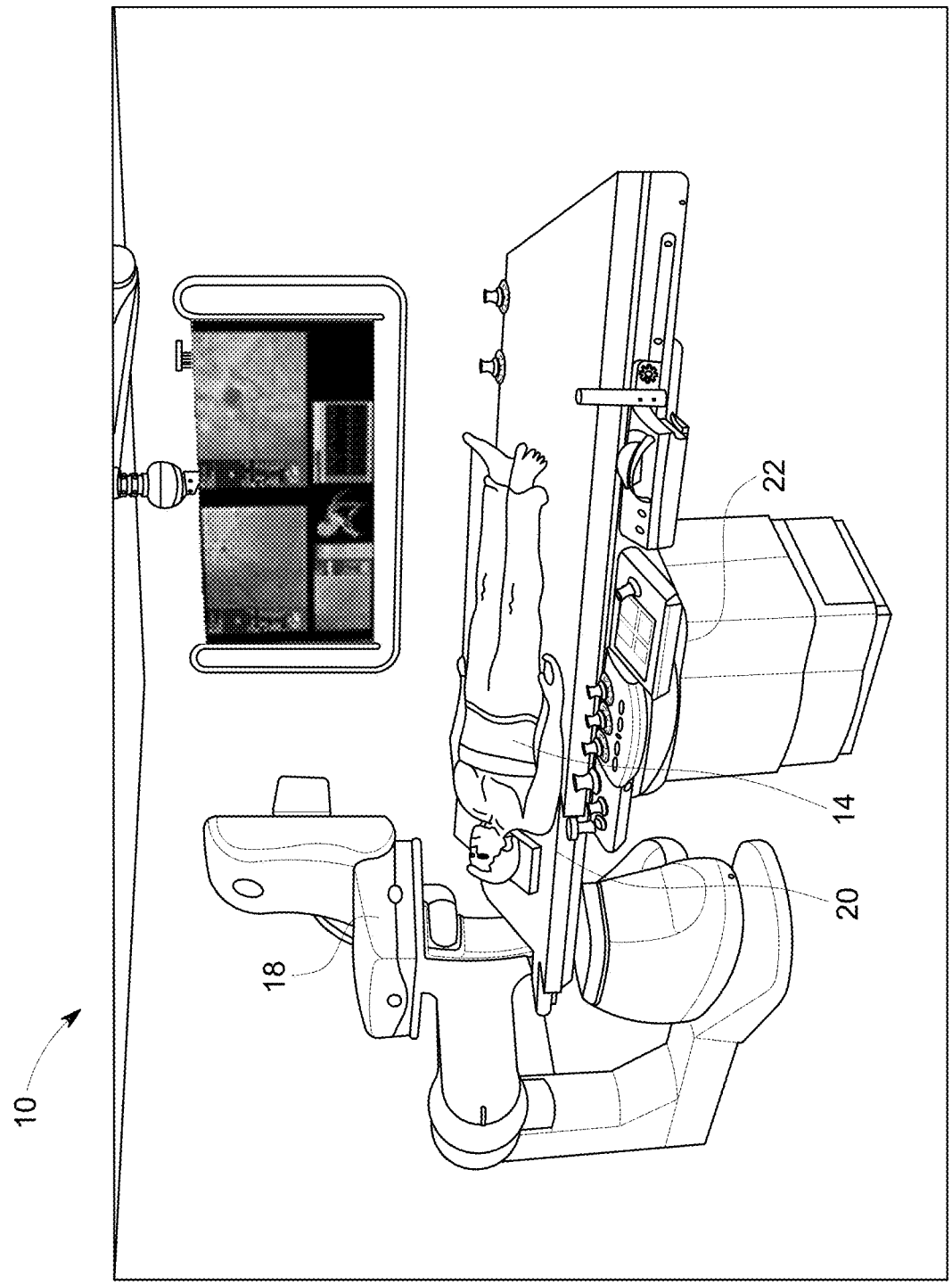
FIG. 1 is a perspective view of a system for simulating bilateral injection of contrast agent into a patient, in accordance with an embodiment of the present invention.
Figure 4:
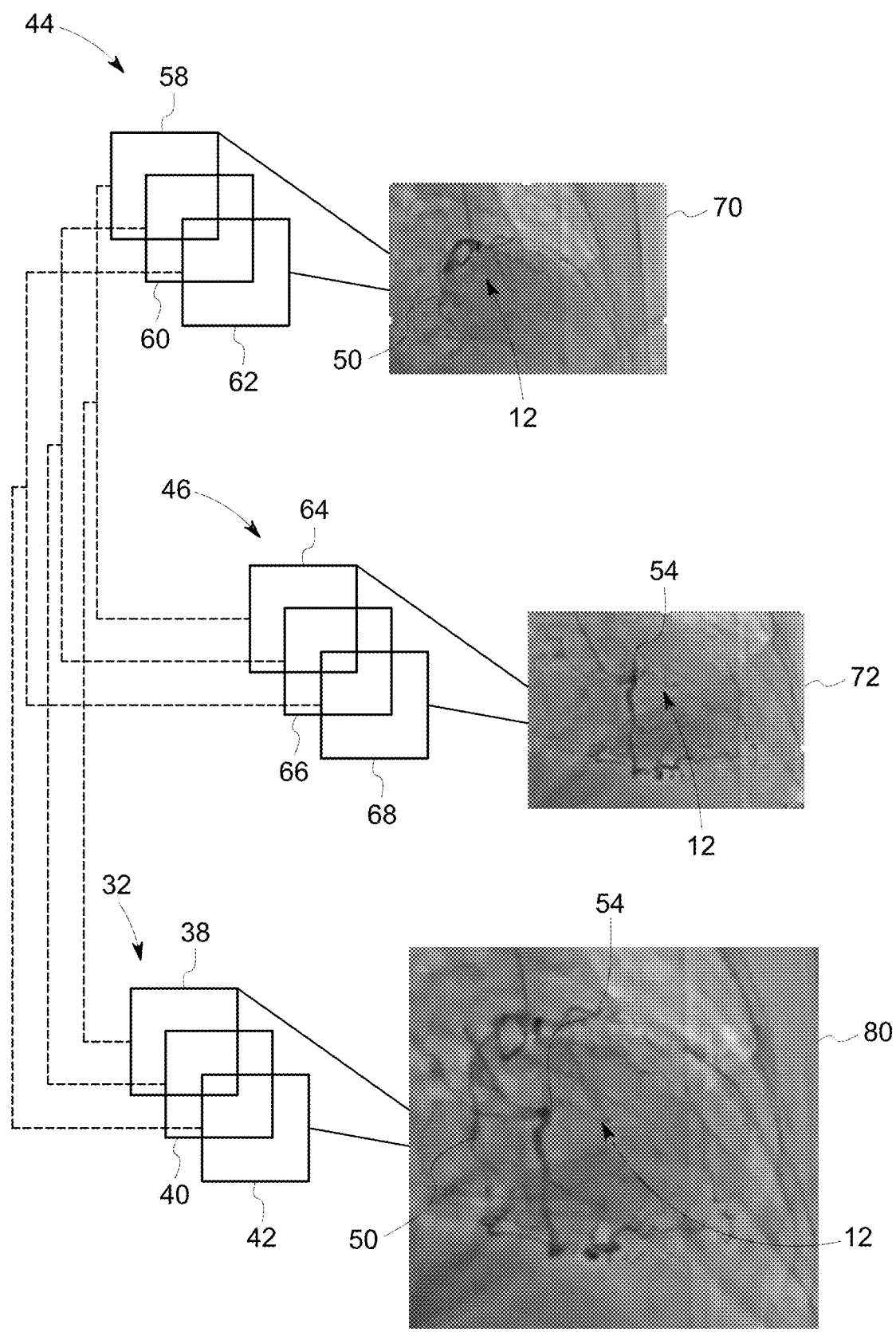
FIG. 4 is a diagram of two image sets acquired via the system of FIG. 1, in accordance with an embodiment of the present invention.
Figure 5:
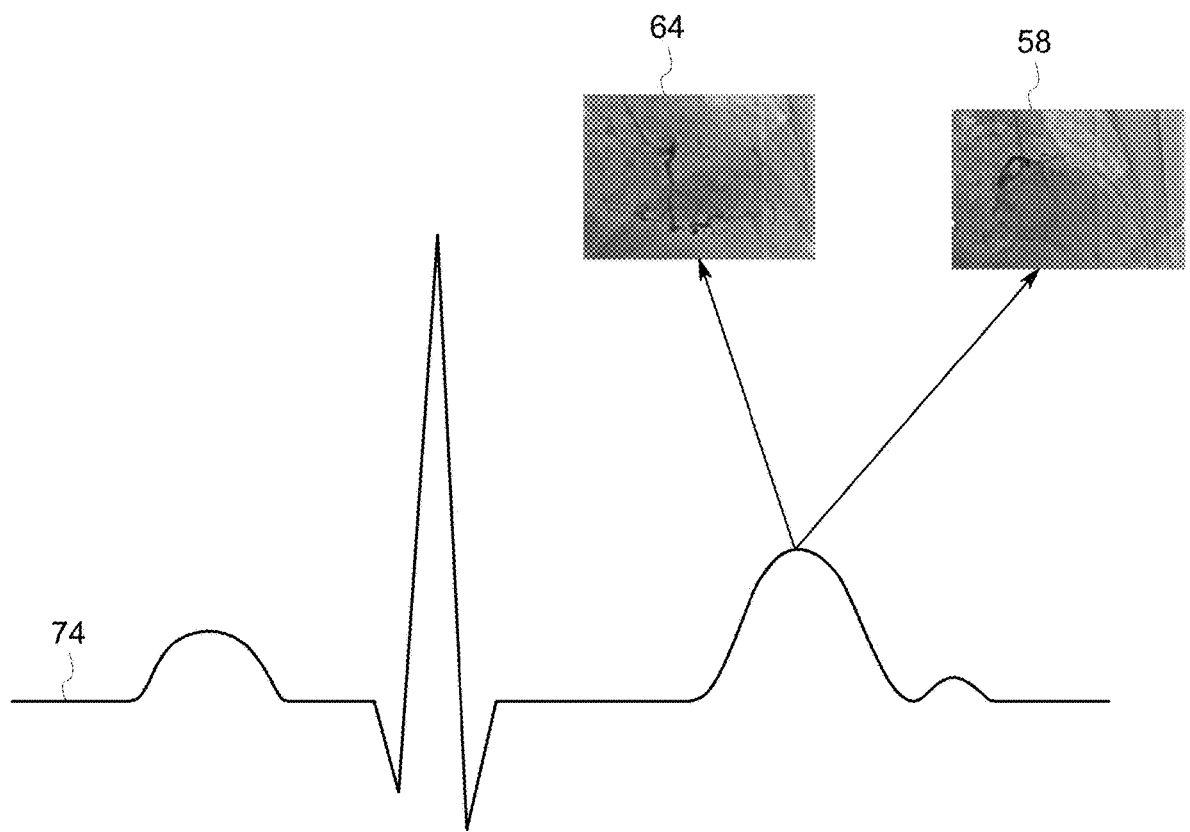
Figure 6:
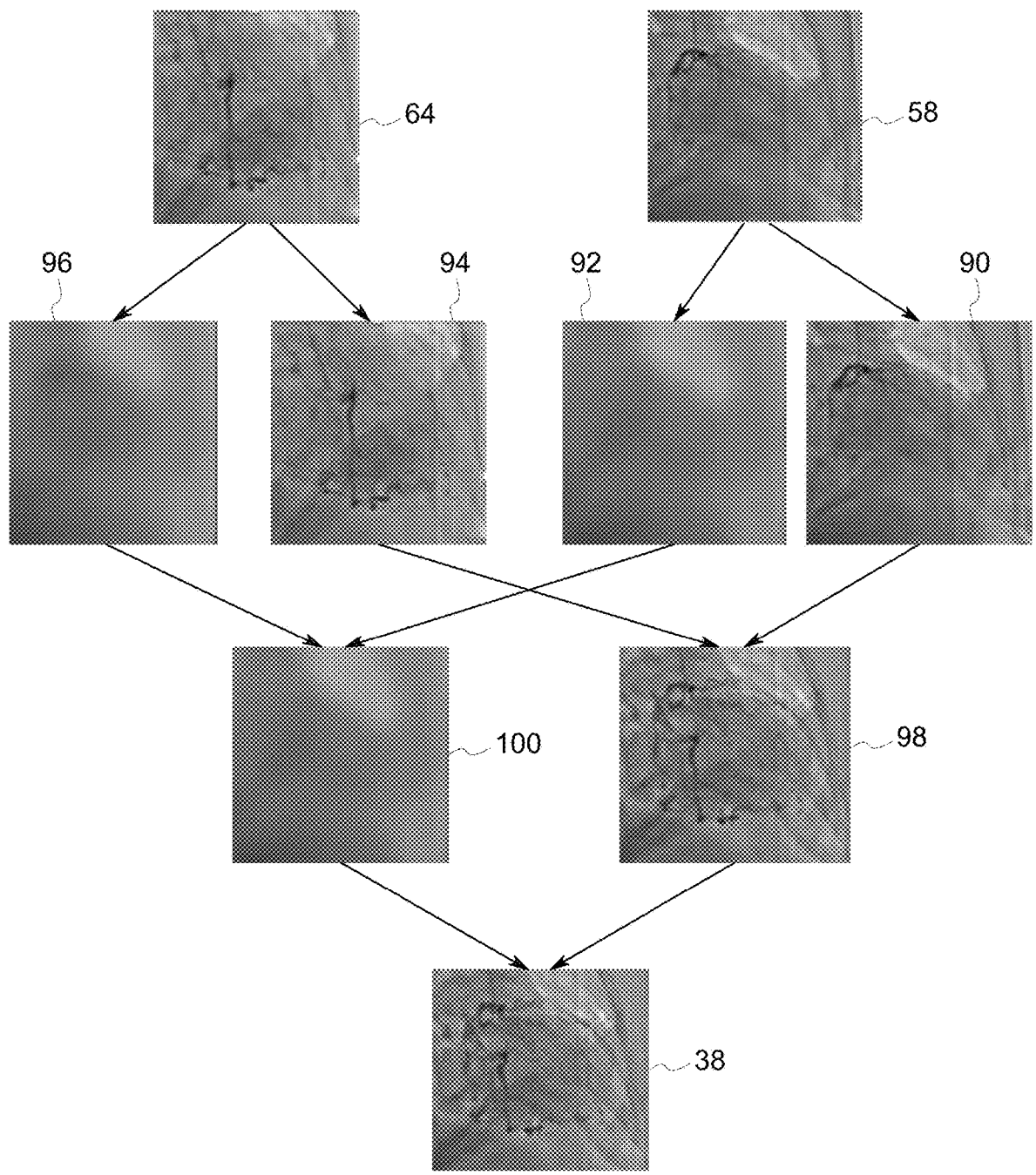

FIG. 5 is a diagram of an image pair of the two image sets of FIG. 4 superimposed over a cardiac cycle of a patient, in accordance with an embodiment of the present invention; and FIG. 6 is a diagram depicting the splitting of an image pair of the two image sets of FIG. 4 into high- and low-frequency components, and combining the high- and low-frequency components into a composite image of a third image set of the system of FIG. 1, in accordance with an embodiment of the present invention.

DETAILED DESCRIPTION

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled," "electrically connected," and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. The term "real-time," as used herein, means a level of processing responsiveness that a user senses as sufficiently immediate or that enables the processor to keep up with an external process. As further used herein, the terms "imaging procedure" and/or "medical imaging procedure" refer to a medical procedure that involves an imaging system to assist in accomplishing one or more tasks. Accordingly, as also used herein, the term "task" means an objective of a medical procedure, e.g., obtaining a biopsy, deploying/installing a stent into a blood vessel, locating an ulcer, imaging a clogged artery, suturing a patient, and/or other medical processes.

Additionally, while the embodiments disclosed herein are described with respect to an x-ray based fluoroscopic imaging system, e.g., an x-ray angiographic imaging system (as shown in FIG. 1), it is to be understood that embodiments of the present invention are equally applicable to other devices such as Computed Tomography ("CT") x-ray imaging systems, Magnetic Resonance Imaging ("MRI") systems, Positron Emission Tomography ("PET"), real-time endoscopic imaging, and/or any other type of imaging system that utilizes contrast agent. As will be appreciated, embodiments of the present invention related imaging systems may be used to analyze objects within any material which can be internally imaged, generally. As such, embodiments of the present invention are not limited to analyzing objects within human tissue.

Referring now to FIG. 1, a perspective view of a system 10 for simulating bilateral injection of contrast agent 12 (FIGS. 2 and 4) into a patient 14 is shown. As will be understood, the system 10 is operative to image one or more structures 16 (FIG. 2), e.g., an internal organ, blood vessel, etc., within the patient 14. For example, the patient 14 may be suffering from one or more blocked coronary arteries, to include a chronic total occlusion, and the imaged structures 16 may be one or more coronary arteries.

Figure 2:
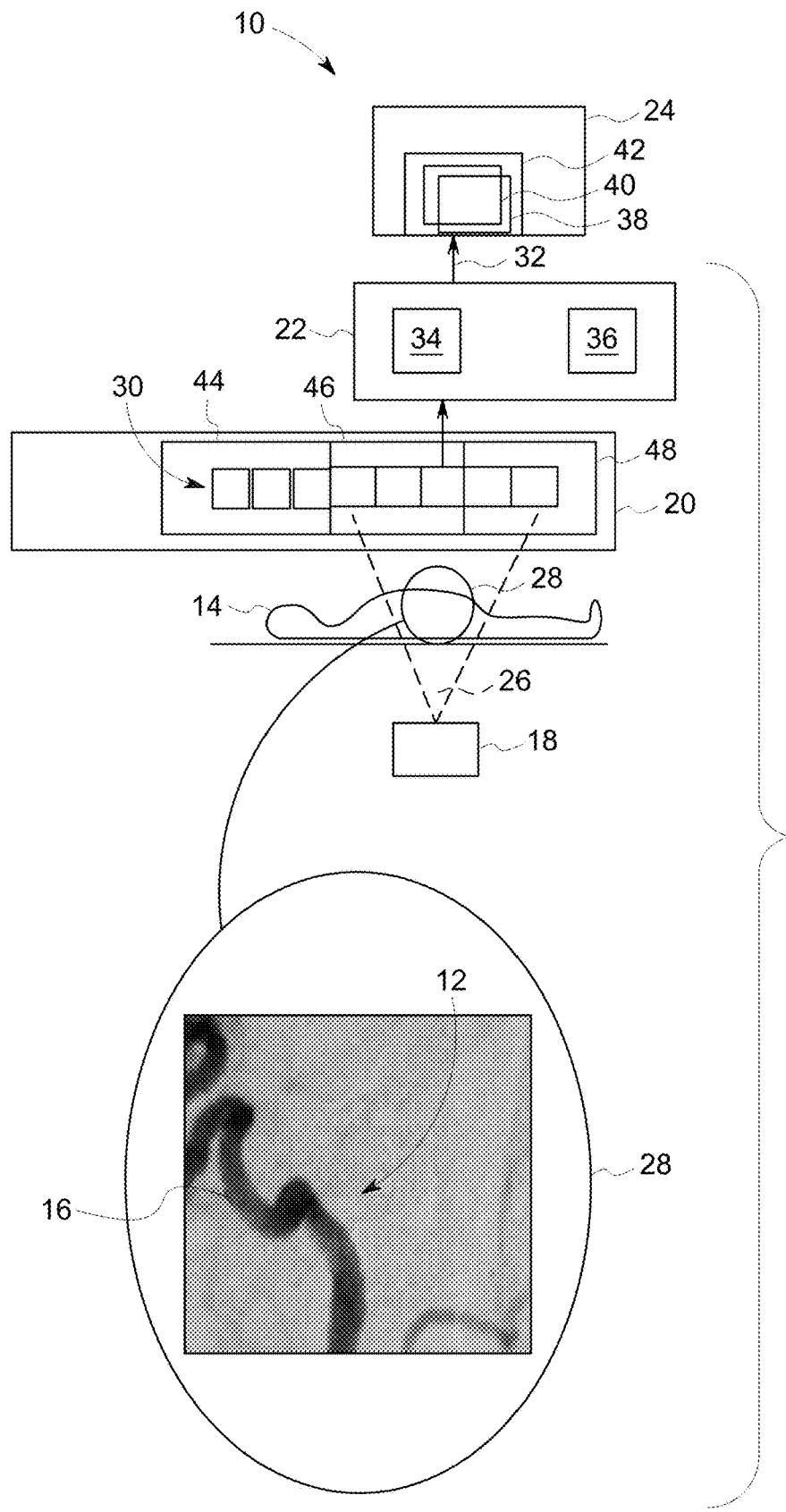
FIG. 2 is a block diagram of the system of FIG. 1, in accordance with an embodiment of the present invention.

Turning to FIG. 2, a block diagram of the system 10 is shown. In embodiments, the system 10 includes: a radiation source/emitter 18 and a detector 20, which collectively form an imaging device, e.g., an x-ray imaging device; a controller 22; and a display screen 24. The radiation source 18 projects a radiation beam 26 through a region of interest ("ROI") 28 of the patient 14 within which the structures 16 are disposed. The radiation beam 26 is received by the detector 20, which generates a plurality of images 30 that are then communicated to the controller 22, which generates a video feed 32 that is transmitted to and displayed by the display screen 24.

As further shown in FIG. 2, the controller 22 includes at least one processor/CPU 34 and at least one memory device 36 and is in electronic communication with the radiation source 18, detector 20, and/or the display screen 24. An imaging program/application may be stored in the at least one memory device 36 that, when loaded into the at least one processor 34, adapts the controller 22 to generate the video feed 32 by processing the images 30 received from the detector 20. In embodiments, the imaging program may further adapt the controller 22 to control the detector 20 and/or the radiation source 18.

The video feed 32 includes a plurality of composite images/frames 38, 40, and 42. The term "composite image", as used herein, means an image generated from two or more other images. For instance, in embodiments, a single composite image 42 may be generated by registering one or more of the acquired images 30 to a reference image selected from the plurality of images 30. The registration of one or more images 30 to a reference image may increase the contrast of the structure 16 within the produced/generated composite image 42. Accordingly, in embodiments, each composite image 38, 40, and 42 may be based at least in part on two or more of the images 30 received by the controller 22 from the detector 20. Once a composite image 42 has been generated, it is transmitted, as part of the video feed 32, by the controller 22 to the display screen 24. In other words, in embodiments, the displayed video feed 32 is a processed form of the raw images 30 acquired by the system 10. In embodiments, the video feed 32 may be a live/real-time and/or near-real-time feed. In other embodiments, one or more of the composite images 38, 40, and 42 may be still images, e.g., a photograph.

As will be understood, the system 10 may acquire one or more images 30 as part of an image set/acquisition 44, 46, 48, wherein the images 30 within the same image set 44, 46, 48 may be acquired between injections of the contrast agent into the patient 14.

Figure 3:
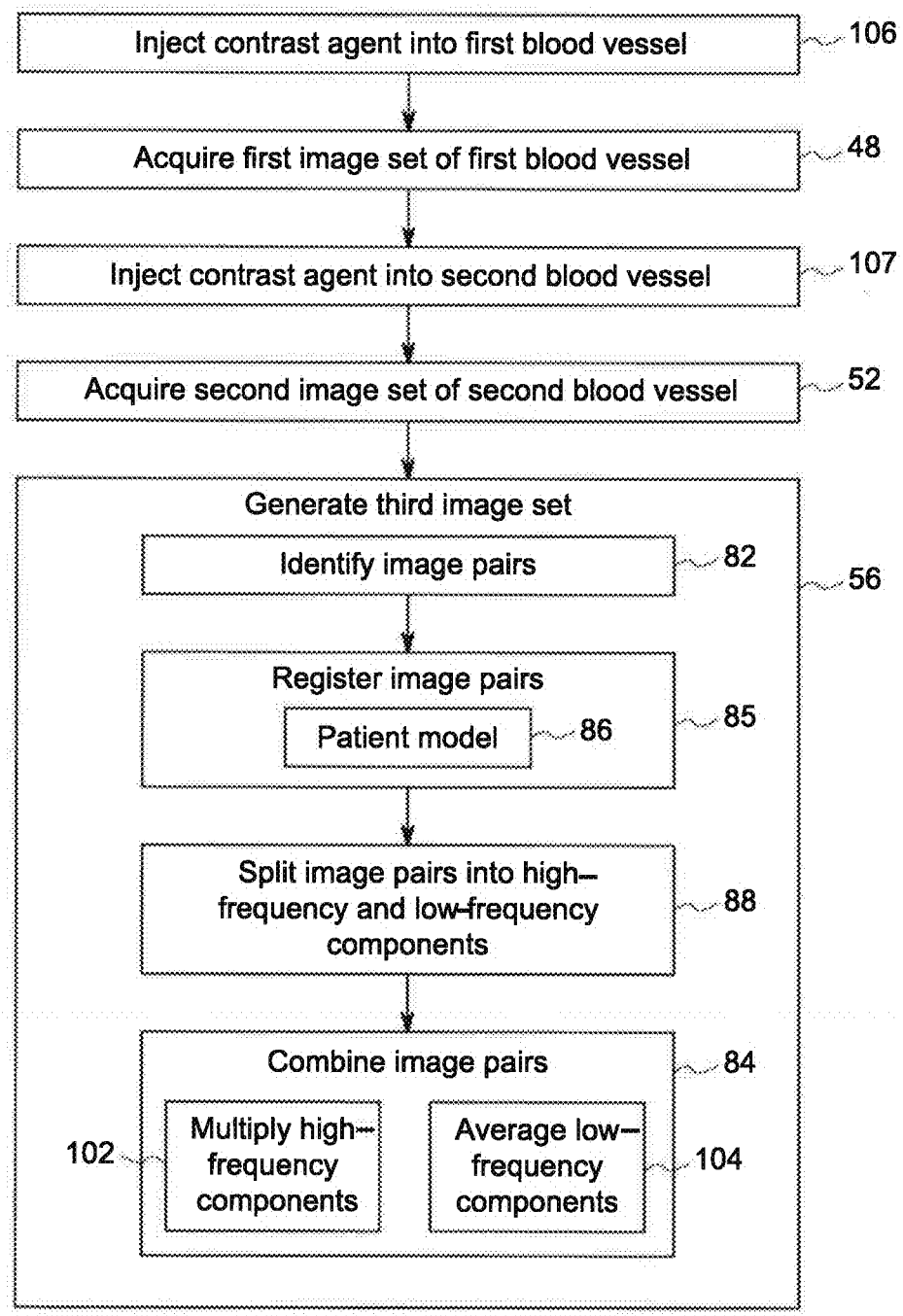
FIG. 3 is a flow chart depicting a method for simulating bilateral injection of contrast agent into a patient utilizing the system of FIG. 1, in accordance with an embodiment of the present invention.

Turning now to FIGS. 3 and 4, in embodiments, the controller 22 (FIGS. 1 and 2) is operative to: acquire 48 a first image set 44 of a first blood vessel 50 having contrast agent 12 therein and disposed in the patient 14 (FIGS. 1 and 2) via the x-ray imaging device 18, 20; acquire 52 a second image set 46 of a second blood vessel 54 having contrast agent 12 therein and disposed in the patient 14 via the x-ray imaging device 18, 20; and generate 56 a third image set 32, e.g., the video feed, based at least in part on the first image set 44 and the second image set 46. As will be appreciated, the third image set 56 includes at least one composite image that depicts both the first blood vessel 50 and the second blood vessel 54.

For example, the two exemplary image sets 44 and 46 shown in FIG. 4 each include three images, e.g., image set 44 includes images 58, 60 and 62; and image set 46 includes images 64, 66 and 68. While the examples disclosed herein depict three images per an image set, it will be understood that, in embodiments, the image sets may include any number of images. Additionally, for the sake of clarity, boxes 70 and 72 symbolically represent a generic depiction of the contents of the images in the first 44 and second 46 image sets, respectively. Accordingly, in embodiments, the first image set 44 may depict the flow of contrast agent 12 within an occluded coronary artery 50 acquired during a first injection of contrast agent 12 via a catheter inserted into the occluded coronary artery 50, and the second image set 46 may depict the flow of contrast agent within an unblocked coronary artery 54 acquired during a second injection of contrast agent via a catheter inserted into the unblocked coronary artery 54. As can be seen in box 72, portions of the occluded coronary artery 50 are visible in the second image set 46 due to so some contrast agent 12 injected into the unblocked coronary artery 54 flowing into the occluded coronary artery 50 via one or more collateral arteries connecting the two. The third exemplary image set 32, i.e., the image set shown on screen 24 in FIG. 2, has three composite images 38, 40 and 42. Similar to boxes 70 and 72, box 80 symbolically represents a generic depiction of the contents of the images in the third image set 32.

Having acquired the first 44 and second 46 image sets, in embodiments, the controller 22 may then generate 56 the third image set 32 by identifying 82 one or more image pairs, each including a first image from the first image set and a second image from the second image set, and for each image pair, combining 84 the first image and the second image of the image pair to produce a composite image. For example, as shown in FIG. 4, the controller 22 may identify 82 the following image pairs: 58 and 64; 60 and 66; and 62 and 68. The controller 22 may then combine 84: images 58 and 64 to generate composite image 38; images 60 and 66 to generate composite image 40; and images 62 and 68 to generate composite image 42.

In certain aspects, an image pairing algorithm is involved in the management of the timing, e.g., cardiac cycle phase alignment, of the two sequences 44 and 46. An image pair may be formed only if the two images are in the same, or approximately close, cardiac phase as estimated from a patient ECG. If the patient's ECG is not recorded along with the image sets, it may be estimated by analyzing the content of the images in the sets 44 and/or 46. In particular, the level of opacification along the sequence may be determined by applying vessel detection algorithms and, from the obtained result, a signal can be derived which represents the opacification of the vessels. Using these different elements, pairs of images having an image of each sequence are formed. The set of pairs may also respect the temporal constraints, i.e., looking at any of the image pairs, the images from the first set 44 shall be in the same temporal order as the images of the second set 46.

Accordingly, turning briefly to FIG. 5, a line 74 representing a single cardiac cycle of the patient's 14 (FIGS. 1 and 2) heart is shown. As will be appreciated, in embodiments, both images in a given image pair may correspond to the same cardiac phase. For example, as shown in FIG. 4, images 58 and 64 may each have been acquired during the t-wave of different cardiac cycles, with the other images pairs, e.g., 60 and 66 (FIG. 4); and 62 and 68 (FIG. 4), each corresponding to other cardiac phases, e.g., p-waves, QRT complexes, ST segment, etc.

Returning back to FIGS. 3 and 4, in embodiments, some geometrical differences may exist between the images in each image pair if the two acquired image sets 44 and 46 have not been acquired with the same imaging settings. Thus, the controller 22 (FIGS. 1 and 2) may be further operative to, for each of the image pairs: 58 and 64; 60 and 66; and 62 and 68, register 85 the images to each other. As the image sets 44 and 46 are likely to have slightly offset views from one another, in embodiments, registering 85 the image pairs may be based at least in part on a three-dimensional ("3D") model 86 that estimates the anatomy of the patient 14 (FIGS. 1 and 2) as one or more planes. For example, in embodiments, the acquired x-ray images, e.g., sets 44 and/or 46, can be modeled as conic projections.

The 3D model 86, as disclosed herein, may start from the hypothesis that the important part of the considered anatomy lays in a plane. By selecting, a priori, a plane as close as possible to the location of the real anatomy, the model 86 can substantially compensate/correct for geometrical differences. As will be understood, the transformation between two different conic projections of a plane is a homographic transform. Therefore, a correction can be made by determining the homographic transform system parameters that indicate the position of the image chain and a corresponding parameter table. In embodiments, the corresponding parameter table may be a set of parameters that describes the orientation of the image chain formed by the radiation emitter/source 18, e.g., x-ray tube, and the detector 20, to include key parameters such as the pixel size for the pixel units of the detector 20, and the distance from the source 18 to the detector 20. In embodiments, the corresponding parameter table may also include parameters describing the position and/or the orientation of the table itself with respect to the image chain, e.g., a description of the position of the table as a group of three (3) translation parameters and three (3) rotational angles.

As will be explained in greater detail below, once an image pair has been formed and appropriate geometric corrections applied, the dynamics of the generated image may be obtained by doing a spatial frequency decomposition of the two images. As used herein with respect to an image, the term "frequency" is to be given its meaning as used in Fourier analysis theorem, which states that any function may be described as the sum of periodic functions whose period defines a frequency. Accordingly, some embodiments of the present invention make a highly simplified use of the frequency properties of images to describe the images in two bands: low and high, wherein a low-frequency band conveys information which varies spatially at a slow pace, and a high-frequency band conveys information which varies spatially at a high pace.

For example, in embodiments, this above-mentioned frequency analysis may be accomplished according to a multiplicative operator. As will be appreciated, the use of a multiplicative operator is based, in part, by the physics of x-ray acquisition as described by the Beer-Lambert law, which is extendable to decompose in thinner frequency bands. Accordingly, the high-frequency images may be successively recombined with a multiplicative operator to the obtained recombined low-frequency images. As such, some embodiments may vary the amount of contrast agent from one injection to the other so as to create fading in and/or fading out effects. Additionally, in some embodiments, the produced images may be generated in color and/or via the same mechanism to render the different injections with different coloring strategies.

As will be understood, the low spatial frequency band of an image can be considered as containing mostly the anatomical background, e.g., spine, ribs, edge of cardiac envelope, etc. Thus, in embodiments in which the aforementioned 3D model 86 was used to correct geometric differences between the two images of an image pair, the two low-frequencies images split out from the images of the image pair may be recombined via averaging. As will be appreciated, the averaging of the low-frequencies of an image pair results in an approximate representation of the anatomical background while avoiding disturbing artifacts that may be created by other image combination methods.

Thus, as discussed above and as further shown in FIG. 3, in embodiments, the controller 22 (FIGS. 1 and 2) may be operative to, for each image pair, 58 and 64 (FIG. 4); 60 and 66 (FIG. 4); and 62 and 68 (FIG. 4) split 88 both images into high-frequency components and low-frequency components, with the controller combining the images for each image pair based at least in part on the high-frequency components and the low-frequency components corresponding to the images of that image pair.

For example, illustrated in FIG. 6 is the frequency decomposition and recombination of image pair 58 and 64. As shown, the controller 22 may split image 58 into its high-frequency component 90 and its low-frequency component 92. The controller 22 may then similarly split image 64 into its high-frequency component 94 and low-frequency component 96. The controller 22 (FIGS. 1 and 2) may then combine the high-frequency components 90 and 94, symbolically depicted by box 98, and/or combine the low-frequency components 92 and 96, symbolically depicted by box 100. As shown in FIG. 3, the high-frequency components 90 and 94 may be combined via multiplication 102, i.e., box 98 depicts the product of the pixel and/or signal values of the high-frequency components 90 and 94. As also shown in FIG. 3, the low-frequency components 92 and 96 may be combined via averaging 104, i.e., box 100 depicts the average of the pixel and/or signal values of the low-frequency components 92 and 96. The combined high-frequency components 98 may then be combined with the combined low-frequency components 100 to generate composite image 38. While FIG. 6 depicts the generation of a single composite image 38 of the third image set 32 from a single image pair 58 and 64, it is to be understood that the controller 22 may process the other identified image pairs, e.g., 60 and 66; and 62 and 68, in the same and/or similar manner to respectively generate additional composite images, e.g., 40 and 42.

Thus, in operation, in accordance with an embodiment, an operator and/or the controller 22 may inject 106 contrast agent 12 into the first blood vessel 50 via a catheter and acquire 48 the first image set 44. After acquisition 48 of the first image set 44, the operator and/or controller 22 may then inject 107 the second blood vessel 54 with contrast agent 12 via another catheter and acquire 52 the second image set 46. After acquisition 52 of the second image set 46, the controller 22 then generates 56 the video feed 32 as described above such that the video feed 32 depicts both blood vessels 50 and 54 at the same time in the same feed and/or in cardiac phase synchronization. As will be appreciated, the video feed 32 can be saved and/or transmitted and played on subsequent screens, e.g., 24 in FIG. 2, to include mobile electronic devices and/or workstations, for viewing by a physician in order to prepare a retrograde navigation in order to mitigate, e.g., stent, punch through, the occlusion in the blocked coronary artery 50.

Additionally, in embodiments, the controller 22 may detect and compensate for respiratory motion of the patient 14. In such embodiments, the controller 22 may detect the patient's 14 respiratory cycle by detecting translations of one or more of the blood vessels 50 and/or 54 between images in one of the image sets 44, 46 and/or 32. In certain aspects, the controller 22 may detect the patient's 14 respiratory cycle by detecting translations of one or more of the blood vessels 50 and/or 54 in one or more of the high-frequency components 90 and/or 94 and/or combined high-frequency components 98.

Finally, it is also to be understood that the device/system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the device/system may include at least one processor and system memory/data storage structures, which may include random access memory (RAM) and read-only memory (ROM). The at least one processor of the device/system 10 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium", as used herein, refers to any medium that provides or participates in providing instructions to the at least one processor of the device/system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a system for simulating bilateral injection of contrast agent into a patient is provided. The system includes an x-ray imaging device and a controller. The controller is operative to: acquire a first image set of a first blood vessel having contrast agent therein via the x-ray imaging device; acquire a second image set of a second blood vessel having contrast agent therein via the x-ray imaging device; and generate a third image set based at least in part on the first image set and the second image set. The third image set includes at least one composite image that depicts both the first blood vessel and the second blood vessel. In certain embodiments, the controller generates the composite image by: identifying an image pair that includes a first image from the first image set and a second image from the second image set; and combining the first image and the second image. In certain embodiments, both images of the image pair correspond to the same cardiac phase. In certain embodiments, the controller is further operative to register the first image and the second image to each other based at least in part on a three-dimensional model that estimates the anatomy of the patient as one or more planes. In certain embodiments, the controller is further operative to split the first image and the second image into high-frequency components and low-frequency components. In such embodiments, the controller combines the first image and the second image based at least in part on the high-frequency components and the low-frequency components. In certain embodiments, the high-frequency components for the first and second images are multiplied together. In certain embodiments, the low-frequency components for the first and second images are averaged together. In certain embodiments, the controller is further operative to acquire the second image set after the first image set.

Other embodiments provide for a method for simulating bilateral injection of contrast agent into a patient. The method includes injecting a first blood vessel with contrast agent; acquiring a first image set of the first blood vessel via an x-ray imaging device; and injecting a second blood vessel with contrast agent. The method further includes: acquiring a second image set of the second blood vessel via the x-ray imaging device; and generating, via a controller, a third image set based at least in part on the first image set and the second image set. The third image set includes at least one composite image that depicts both the first blood vessel and the second blood vessel. In certain embodiments, generating, via a controller, a third image set based at least in part on the first image set and the second image set includes: identifying an image pair that includes a first image from the first image set and a second image from the second image set; and combining the first image and the second image to produce the composite image. In certain embodiments, the first image and the second image correspond to the same cardiac phase. In certain embodiments, the method further includes registering, via the controller, the first image and the second image to each other based at least in part on a three-dimensional model that estimates the anatomy of the patient as one or more planes. In certain embodiments, combining the first image and the second image includes: splitting the first image and the second image into high-frequency components and low-frequency components; and combining the high-frequency components and the low-frequency components. In certain embodiments, combining the high-frequency components and the low-frequency components includes multiplying together the high-frequency components for the first and second images. In certain embodiments, combining the high-frequency components and the low-frequency components includes averaging together the low-frequency components for the first and second images. In certain embodiments, the second blood vessel is injected with contrast agent after acquisition of the first image set.

Yet still other embodiments provide for a non-transitory computer readable medium storing instructions. The stored instructions adapt a controller to: acquire a first image set of a first blood vessel having contrast agent therein; acquire a second image set of a second blood vessel having contrast agent therein; and generate a third image set based at least in part on the first image set and the second image set. The third image set includes at least one composite image that depicts both the first blood vessel and the second blood vessel. In certain embodiments, the stored instructions further adapt the controller to generate the third image set by: identifying an image pair that includes a first image from the first image set and a second image from the second image set; and combining the first image and the second image to produce the composite image. In certain embodiments, the stored instructions further adapt the controller to: register the first image and the second image to each other based at least in part on a three-dimensional model that estimates the anatomy of the patient as one or more planes. In certain embodiments, the stored instructions further adapt the controller to split the first and second images into high-frequency components and low-frequency components. In such embodiments, the controller combines the first and second images based at least in part on the high-frequency components and the low-frequency components.

Accordingly, as will be appreciated, by combining two image sets into a third image set, some embodiments of the present invention provide for the staggering, i.e., occurring at different times, of contrast agent injections into the coronary arteries of a patient while providing a physician with an image set that simulates bilateral injection of coronary arteries with contrast agent. In other words, some embodiments of the present invention provide for an image set that gives the appearance of two coronary arteries being injected at the same time, i.e., a bilateral injection, when, in fact, the coronary arteries may be injected at different times.

Moreover, by synchronizing and/or correcting for geographic difference between image pairs, i.e., registering the images in an image pair to each other, some embodiments of the present invention provide for improved visualization of collateral arteries connecting two coronary arteries and, accordingly, for improved planning of guidewire paths for retrograde navigations, over traditional side by side analysis of two separate video feeds of two staggered injections of contrast agent.

As will be further appreciated, staggering contrast agent injections improves the overall workflow of imaging a Chronic Total Occlusion in preparation for a retrograde navigation to remove the occlusion, as the physician need only guide one catheter at a time, as opposed to simultaneously managing two separate catheters in two different coronary arteries.

Yet further still, the generated/combined video feed/image set of some embodiments may be merged with and/or superimposed onto a live feed of a fluoroscopic image sequence and/or other type of medical imaging procedure.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A system for simulating bilateral injection of contrast agent into a patient, the system comprising:
    an x-ray imaging device; and
    controller operative to:
        acquire a first image set of a first blood vessel having contrast agent therein via the x-ray imaging device, wherein the first image set includes a first image;
        acquire a second image set of a second blood vessel having contrast agent therein via the x-ray imaging device, wherein the second image set includes a second image;
        split the first image and the second image into high-frequency components and low-frequency components;
        generate a composite image that depicts both the first blood vessel and the second blood vessel by combing the first image and the second image based at least in part on the high-frequency components and the low-frequency components; and
        generate a third image set based at least in part on the first image set and the second image set, wherein the third image set includes the composite image.

2. The system of claim 1, wherein the first image and the second image correspond to a same cardiac phase.

3. The system of claim 1, wherein the controller is further operative to:
    register the first image and the second image to each other based at least in part on a three-dimensional model that estimates the anatomy of the patient as one or more planes.

4. The system of claim 1, wherein the high-frequency components for the first and second images are multiplied together.

5. The system of claim 1, wherein the low-frequency components for the first and second images are averaged together.

6. The system of claim 1, wherein the controller is further operative to acquire the second image set after the first image set.

7. A method for simulating bilateral injection of contrast agent into a patient, the method comprising:
    injecting a first blood vessel with contrast agent;
    acquiring a first image set of the first blood vessel via an x-ray imaging device, wherein the first image set includes a first image;
    injecting a second blood vessel with contrast agent;
    acquiring a second image set of the second blood vessel via the x-ray imaging device, wherein the second image set includes a second image; and
    splitting the first image and the second image into high-frequency components and low-frequency components;
    generating a composite image that depicts both the first blood vessel and the second blood vessel by combing the first image and the second image, wherein combing the first image and the second image includes combining the high-frequency components and the low-frequency components; and
    generating, via a controller, a third image set based at least in part on the first image set and the second image set, wherein the third image set includes the composite image.

8. The method of claim 7, wherein the first image and the second image correspond to a same cardiac phase.

9. The method of claim 7 further comprising:
    registering, via the controller, the first image and the second image to each other based at least in part on a three-dimensional model that estimates the anatomy of the patient as one or more planes.

10. The method of claim 7, wherein combining the high-frequency components and the low-frequency components comprises:
    multiplying together the high-frequency components for the first and second images.

11. The method of claim 7, wherein combining the high-frequency components and the low-frequency components comprises:
    averaging together the low-frequency components for the first and second images.

12. The method of claim 7, wherein the second blood vessel is injected with contrast agent after acquisition of the first image set.

13. A non-transitory computer readable medium storing instructions that adapt a controller to:

acquire a first image set of a first blood vessel having contrast agent therein, wherein the first image set includes a first image;

acquire a second image set of a second blood vessel having contrast agent therein, wherein the second image set includes a second image;

split the first image and the second image into high-frequency components and low frequency components;

generate a composite image that depicts both the first blood vessel and the second blood vessel by combining the first image and the second image based at least in part on the high-frequency components and the low-frequency components;

generate a third image set based at least in part on the first image set and the second image set, wherein the third image set includes at least one composite image that depicts both the first blood vessel and the second blood vessel.

14. The non-transitory computer readable medium of claim 13, wherein the stored instructions further adapt the controller to:

register the first image and the second image to each other based at least in part on a three-dimensional model that estimates the anatomy of the patient as one or more planes.

* * * * *